United States Patent [19]
Sano et al.

[11] Patent Number: 5,974,884
[45] Date of Patent: Nov. 2, 1999

[54] ULTRASONIC DIAGNOSTIC APPARATUS AND ULTRASONIC PROBE WITH ACOUSTIC MATCHING LAYER HAVING CONTINUOUSLY VARIED ACOUSTIC IMPEDANCE IN THE THICKNESS DIRECTION

[75] Inventors: Shuzo Sano, Kashiwa; Mikio Izumi, Soka, both of Japan

[73] Assignee: Hitachi Medical Corporation, Tokyo, Japan

[21] Appl. No.: 09/154,697

[22] Filed: Sep. 17, 1998

[30] Foreign Application Priority Data

Sep. 19, 1997 [JP] Japan .................................. 9-255054

[51] Int. Cl.$^6$ .................................................. G01N 29/00
[52] U.S. Cl. .................................. 73/589; 73/588; 73/629
[58] Field of Search ............................. 73/579, 589, 618, 73/620, 626, 627, 628, 866.5, 642, 632, 644; 310/311, 313, 320, 321, 327, 335, 334, 336; 600/437, 444, 443, 447, 459, 472

[56] References Cited

U.S. PATENT DOCUMENTS

| 4,571,520 | 2/1986 | Saito et al. ............................ 310/327 |
| 5,115,809 | 5/1992 | Saitoh et al. ...................... 128/662.03 |
| 5,142,187 | 8/1992 | Saito et al. ............................ 310/358 |
| 5,212,671 | 5/1993 | Fujii et al. ............................. 367/151 |

Primary Examiner—Hezron Williams
Assistant Examiner—Thuy Vinh Tran
Attorney, Agent, or Firm—Antonelli, Terry, Stout & Kraus, LLP

[57] ABSTRACT

In an ultrasonic probe, an acoustic matching layer, which is fixed on the front side of a transducer for transmitting an ultrasonic wave and receiving a reflected wave thereof and matches in acoustic impedance the transducer to a living tissue in an object to be examined, is formed in such a structure that the acoustic impedance thereof is varied continuously in the thickness direction from the transducer to the object to be examined.

10 Claims, 13 Drawing Sheets

FIG. 10

① A PLURALITY OF TAPERED POLE-LIKE ELEMENTS ARE FORMED USING FIRST ACOUSTIC MATCHING MATERIAL

↓

② SPACES AMONG THE PLURALITY OF TAPERED POLE-LIKE ELEMENTS ARE FILLED WITH SECOND ACOUSTIC MATCHING METERIAL, AND THEN THE SECOND ACOUSTIC MATCHING MATERIAL IS HARDENED

↓

③ BY ACHIEVING THE FINISHING UP TO A PREDETERMINED THICKNESS, AN ACOUSTIC MATCHING LAYER IS COMPLETED

↓

④ THE ACOUSTIC MATCHING LAYER IS FIXED ON THE FRONT SIDE OF A TRANSDUCER

FIG. 11A 

FIG. 11B 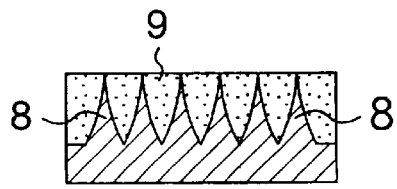

FIG. 11C 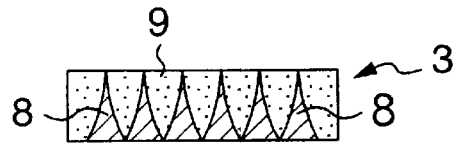

ULTRASONIC DIAGNOSTIC APPARATUS AND ULTRASONIC PROBE WITH ACOUSTIC MATCHING LAYER HAVING CONTINUOUSLY VARIED ACOUSTIC IMPEDANCE IN THE THICKNESS DIRECTION

BACKGROUND OF THE INVENTION

In connection with an ultrasonic diagnosis technology which, using an ultrasonic wave, allows ultrasonic images to be obtained concerning a diagnosis part in an object to be examined, the present invention relates to an ultrasonic probe which, by broadening employed frequency bandwidth, makes it possible to enhance an efficiency in the ultrasonic diagnosis, a method of manufacturing thereof, and an ultrasonic diagnostic apparatus using the ultrasonic probe.

A prior art ultrasonic probe comprised a transducer which transmits an ultrasonic wave and receives the reflected wave, a cable connected with an electrode of the transducer, and an acoustic matching layer which is fixed on the front side of the above-mentioned transducer and matches, in acoustic impedance, the transducer to a living tissue in the object such as a human body to be examined. Moreover, the above-described acoustic matching layer was formed in, for example, a one layer or two layers of seat-like form. On account of this, matching conditions for the acoustic impedance were determined so that, for a specific frequency of the ultrasonic wave generated by the transducer, the ultrasonic wave can effectively be transmitted to and received from the diagnosis part.

Concretely, matching conditions for the above-described two layers of seat-like acoustic matching layer are presented on pages 20 to 30 in "TRANSACTION ON SONICS AND ULTRASONICS" VOL. SU-13, NO. 1 (MARCH, 1966): When the central frequency of the transducer is 2.5 MHz and the acoustic impedance thereof is 28 MRayl, the first acoustic matching layer is formed with the acoustic impedance of about 8 MRayl and the film thickness which is one-quarter wavelength thick to the above-mentioned central frequency, and the second acoustic matching layer is formed with the acoustic impedance of about 2 MRayl and the film thickness which is, equally, one-quarter wavelength thick thereto.

In such a prior art ultrasonic probe, since the acoustic matching layer was formed in the one layer or two layers of seat-like form with the film thickness which is one-quarter wavelength thick to the central frequency of the transducer, matching conditions for the acoustic impedance were determined so that ultrasonic waves are effectively transmitted and received for only a specific frequency thereof. Accordingly, in the prior art ultrasonic probe, as shown in FIG. 19, the signal intensity distribution was narrower as compared with the employed frequency bandwidth. This limited a frequency bandwidth through which the ultrasonic waves are able to pass effectively and made it almost impossible for them to pass through a frequency bandwidth being off the central frequency, thus limiting frequencies available for the ultrasonic probe. Consequently, when performing diagnoses such as a pathological diagnosis of a patient with the use of one and the same ultrasonic diagnostic apparatus, the ultrasonic probe to be used therein had to be replaced depending on the following cases: Namely, for example, when observing a cross sectional image with a wide visual field, an ultrasonic probe for a low frequency had to be used, when observing a cross sectional image with a high resolution, an ultrasonic probe for a high frequency had to be used, and further when observing a bloodstream image by means of Doppler measurement, an ultrasonic probe for another frequency had to be used. This situation brought about a low efficiency in the ultrasonic diagnosis and at the same time resulted in a problem that there had to be prepared a lot of and many kinds of these ultrasonic probes.

SUMMARY OF THE INVENTION

Accordingly, it is an object of the present invention to provide an ultrasonic probe which, so as to deal with such problems and by broadening employed frequency bandwidth, makes it possible to enhance an efficiency in the ultrasonic diagnosis, a method of manufacturing thereof, and an ultrasonic diagnostic apparatus using the ultrasonic probe.

In order to attain the above-mentioned object, an ultrasonic probe according to the present invention comprises a transducer which transmits an ultrasonic wave and receives the reflected wave, a cable connected with an electrode of the transducer, and an acoustic matching layer which is fixed on the front side of the above-mentioned transducer and matches, in acoustic impedance, the transducer to a living tissue in an object to be examined, the above-described acoustic matching layer being formed in such a structure that the acoustic impedance thereof is varied continuously in the thickness direction.

Also, the structure of the above-mentioned acoustic matching layer is as follows: Employed are first acoustic matching material, the acoustic impedance of which is equal to or lower than that of the transducer, and second acoustic matching material, the acoustic impedance of which is equal to or higher than that of the living tissue in the object to be examined. Then, a plurality of tapered pole-like elements, which are formed with the above-mentioned first acoustic matching material in such a manner that the cross sectional area thereof or the volume thereof is larger on the side of the transducer and is smaller on the side of the object to be examined, are arranged in a matrix-like form with a spacing shorter than a wavelength of the ultrasonic wave. Next, spaces among the plurality of tapered pole-like elements arranged in the matrix-like form are filled with the second acoustic matching material, thus forming the acoustic matching layer.

Further, the above-described first acoustic matching material is a composite material obtained by mixing a metal or an oxide into a metal, a semiconductor, ceramics, or a resin, and the acoustic impedance thereof is in a range of 10 to 30 MRayl. The second acoustic matching material is a composite material obtained by mixing a metal or an oxide into various kinds of resins or a resin, and the acoustic impedance thereof is in a range of 1.5 to 3 MRayl.

Still further, the plurality of tapered pole-like elements, which are formed with the above-mentioned first acoustic matching material, are formed in a form like a circular cone, a pyramid, or a cone the generator of which is expressed by exponential function or trigonometric functions. Otherwise, the plurality of tapered pole-like elements formed with the first acoustic matching material are formed in the following way: A plurality of plate-like members, which are formed with the first acoustic matching material and the cross sections of which are formed in a serration-like form, an exponential function-like form, or a trigonometric function-like form, are cut with a spacing shorter than a wavelength of the ultrasonic wave, thereby forming the plurality of tapered pole-like elements.

A method of manufacturing the ultrasonic probe as a related invention thereof comprises the following steps: First, the plurality of tapered pole-like elements are formed with the first acoustic matching material, the acoustic impedance of which is equal to or lower than that of the transducer, in such a manner that the cross sectional area thereof or the volume thereof is larger on the side of the transducer and is smaller on the side of the object to be examined, and then the tapered pole-like elements formed are arranged in the matrix-like form with a spacing shorter than a wavelength of the ultrasonic wave. Then, spaces among the plurality of tapered pole-like elements, which are formed with the first acoustic matching material, are filled with the second acoustic matching material the acoustic impedance of which is equal to or higher than that of the living tissue in the object to be examined. Moreover, the second acoustic matching material is hardened, and then the whole structure thus formed is finished to a predetermined thickness, thereby completing the acoustic matching layer. After that, the acoustic matching layer completed is fixed in such a manner as to cover the front side of the transducer.

Another example of a method of manufacturing the above-described ultrasonic probe comprises the following steps: Formed first is a mold for forming the plurality of tapered pole-like elements, which are to be formed in such a manner that the cross sectional area thereof or the volume thereof is larger on the side of the transducer and is smaller on the side of the object to be examined and are arranged in a matrix-like form with a spacing shorter than a wavelength of the ultrasonic wave. Then, by pouring into the mold the first acoustic matching material the acoustic impedance of which is equal to or lower than that of the transducer, the plurality of tapered pole-like elements arranged in the matrix-like form are formed. Next, spaces among the plurality of tapered pole-like elements, which are formed with the first acoustic matching material, are filled with the second acoustic matching material the acoustic impedance of which is equal to or higher than that of the living tissue in the object to be examined. Furthermore, the second acoustic matching material is hardened, and then the whole configuration is finished to a predetermined thickness, thereby completing the acoustic matching layer. After that, the acoustic matching layer completed is fixed on the front side of the transducer.

The ultrasonic diagnostic apparatus as a related invention of the ultrasonic probe comprises the ultrasonic probe which has the transducer for transmitting and receiving ultrasonic wave and the acoustic matching layer in which the acoustic impedance thereof is varied continuously in the thickness direction, an ultrasonic wave transmitting/receiving unit which not only drives the transducer in the ultrasonic probe and causes it to generate the ultrasonic wave but also receives the reflected wave, an image constructing unit for inputting a wave reception signal from the ultrasonic wave transmitting/receiving unit so as to perform the imaging processing, an image memory which not only temporarily stores data from the image constructing unit but also performs the conversion so that an arbitrary display is possible, an image displaying unit for reading image data from the image memory so as to display the image, a frequency selector for causing the ultrasonic wave to be transmitted and received in a specific frequency bandwidth, and a control unit for controlling the above-mentioned constitution components.

In the ultrasonic probe according to the present invention, the acoustic matching layer is formed in such a structure that the acoustic impedance thereof is varied continuously in a direction heading from surface of the transducer to the object to be examined. This prevents a discontinuity in the acoustic impedance, thus giving rise to less reflection of the ultrasonic wave within the acoustic matching layer. Meanwhile, in the acoustic matching layer in the prior art probe, there sometimes occurred the discontinuity. Accordingly, the ultrasonic probe in the present invention makes it possible to effectively transmit and receive ultrasonic wave in a broader frequency bandwidth, thus allowing the employed frequency bandwidth to be broadened. Consequently, it becomes possible to embody, with the use of a single ultrasonic probe, the functions of the plurality of ultrasonic probes which were used specifically for the low frequency, the high frequency, the Doppler measurement, and so on, respectively. This situation necessitates no replacement of an ultrasonic probe to be used, thus making it possible to enhance an efficiency in the ultrasonic diagnosis. Also, there is no need of preparing a lot of and many kinds of those ultrasonic probes, and thus it becomes easier to handle the ultrasonic diagnostic apparatus.

Also, the method of manufacturing an ultrasonic probe according to the present invention, which makes it possible to, in great number and effectively, manufacture the ultrasonic probes which are constituted as above according to the present invention, is suitable for the mass production thereof.

Furthermore, the ultrasonic probe constituted as above is employed as the ultrasonic probe in the ultrasonic diagnostic apparatus according to the present invention. This, as shown in FIG. 18, enables the signal intensity distribution to be broadened as compared with the employed frequency bandwidth. This condition further makes it possible to broaden a frequency bandwidth through which the ultrasonic wave are able to pass effectively and allows them to pass through a frequency bandwidth being off the central frequency, thus enlarging frequencies available for the ultrasonic diagnostic apparatus. Also, providing the frequency selector inside an operation unit, through an operation of the frequency selector, makes it possible to specify what frequency bandwidth the above-described ultrasonic probe is used in. This allows a single ultrasonic probe to be utilized in a broader frequency range without being replaced, although, in the prior art, an ultrasonic probe to be used is replaced one by one depending on differences in the frequency bandwidth employed. Accordingly, it becomes possible to enhance an efficiency in the ultrasonic diagnosis.

BRIEF DESCRIPTION OF THE DRAWINGS

FIG. 10 is a flow chart for explaining a method of manufacturing the ultrasonic probe as a related invention of the above-described ultrasonic probe;

FIGS. 11A to 11C are flow diagrams for illustrating the procedure in FIG. 10;

DESCRIPTION OF THE PREFERRED EMBODIMENTS

Based on the accompanying drawings, the description will be given below in detail concerning an embodiment of the present invention.

Figure 1:
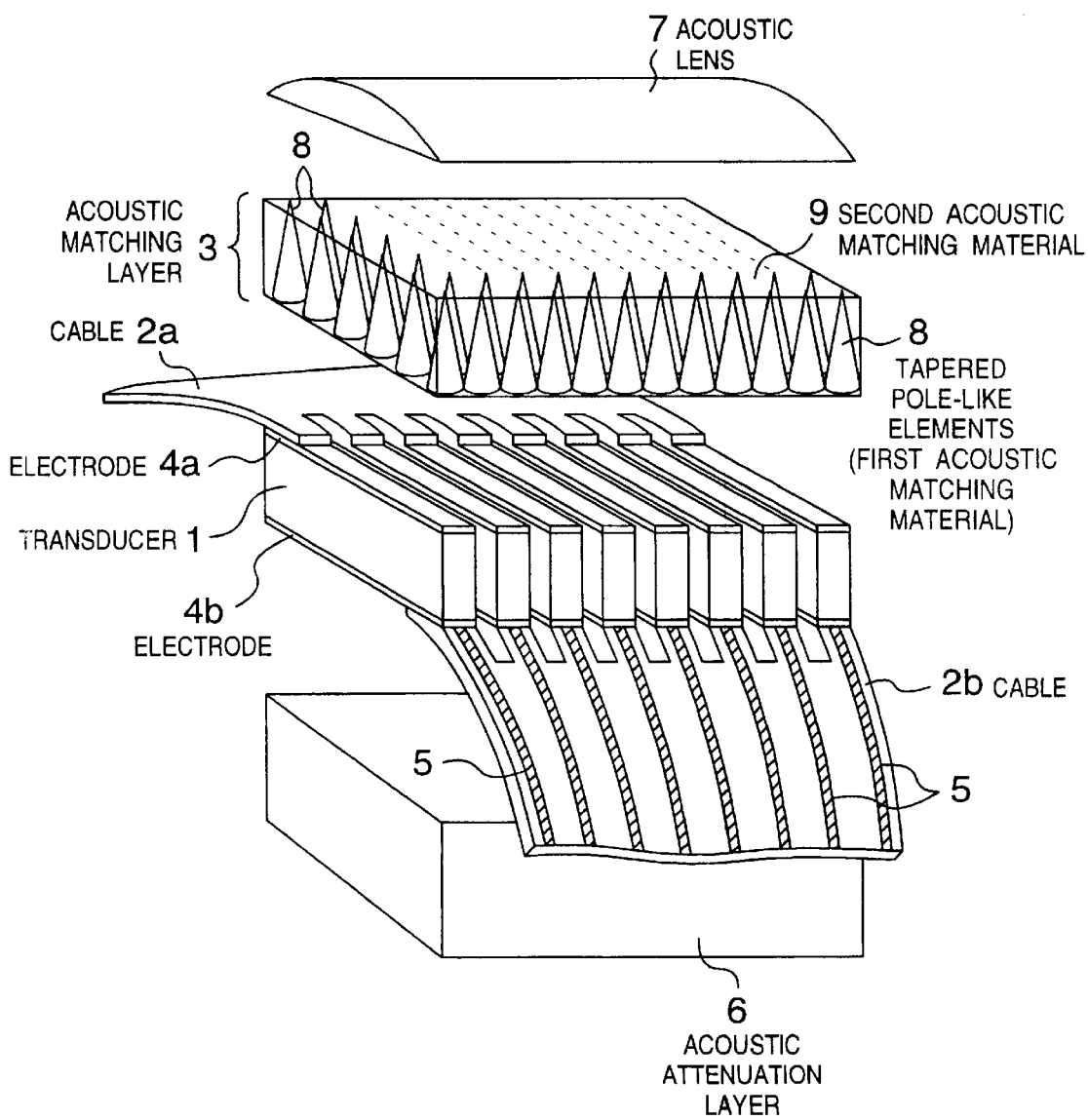
FIG. 1 is a disassembled perspective view for showing an embodiment of an ultrasonic probe according to the present invention.

FIG. 1 is a disassembled perspective view for showing an embodiment of an ultrasonic probe according to the present invention. In an ultrasonic diagnosis technology which, using an ultrasonic wave, allows ultrasonic images to be obtained concerning a diagnosis part in an object to be examined, the ultrasonic probe actually transmits and receives the ultrasonic wave to and from the above-mentioned diagnosis part, and comprises a transducer 1, cables 2a, 2b, and an acoustic matching layer 3, as is shown in FIG. 1.

The above-mentioned transducer 1 transmits the ultrasonic wave and receives the reflected wave, and is composed of a piezoelectric material such as PZT (lead titanate zirconate base porcelain) which performs a conversion between electrical energy and ultrasonic energy. The transducer 1 is constituted by arranging in a row a lot of transducer elements formed in a strip-like shape. Electrodes 4a and 4b for driving the transducer elements are each provided on upper and lower surfaces of each transducer element. These transducer elements are arranged so that the pitch therebetween is shorter than a wavelength of the ultrasonic wave.

The above-mentioned electrodes 4a, 4b are connected with the cables 2a, 2b, respectively. The cables 2a, 2b supply a wave transmission signal from an ultrasonic wave transmission/reception unit, which is not illustrated, and fetch a reflected echo signal received. The cable 2a corresponds to a ground line, and the cable 2b corresponds to a signal line. Additionally, conductors 5, 5, . . . , each of which is connected with each transducer element in the above-mentioned transducer 1, are provided on the cable 2b on the side of the above-described signal line.

Incidentally, an acoustic attenuation layer 6 is provided on the reverse side of the above-described transducer 1. Although the ultrasonic wave is transmitted from the reverse side of the transducer, too, the acoustic attenuation layer 6 prevents it from getting back again to the transducer 1. The acoustic attenuation layer 6, which is composed of a material effective in attenuating an ultrasonic wave, attenuates the ultrasonic wave, thus eliminating acoustic influences on the front side of the transducer 1. Also, an acoustic lens 7 is provided on the front side of the above-described acoustic matching layer 3. The acoustic lens 7 focuses the ultrasonic wave which the transducer 1 transmits towards the front side thereof.

In the present invention, the acoustic matching layer 3 is formed in such a structure that the acoustic impedance thereof is varied continuously in the thickness direction heading from the side of the above-mentioned transducer 1 to the side of the object to be examined (the side of the acoustic lens 7). Namely, as shown in FIG. 1, the structure of the above-mentioned acoustic matching layer 3 is as follows: Employed are first acoustic matching material, the acoustic impedance of which is equal to or lower than that of the transducer 1, and second acoustic matching material 9, the acoustic impedance of which is equal to or higher than that of the living tissue in the human body to be examined. Then, a plurality of tapered pole-like elements 8, 8, . . . , which are formed with the above-mentioned first acoustic matching material in such a manner that the cross sectional area thereof or the volume thereof is larger on the side of the transducer 1 and is smaller on the side of the object to be examined, are arranged in a matrix-like form with a spacing shorter than a wavelength of the ultrasonic wave to be used in correspondence with the above-described transducer elements. Next, spaces among the plurality of tapered pole-like elements 8, 8, . . . , which are arranged in the matrix-like form, are filled with the second acoustic matching material 9, thus forming the acoustic matching layer 3.

Moreover, the first acoustic matching material, with which the above-mentioned tapered pole-like elements 8, 8, . . . are formed, is made of a composite material obtained by mixing a metal or an oxide into a resin or a metal, a semiconductor or ceramics, and the acoustic impedance thereof is set to be in a range of 10 to 30 MRayl. The second acoustic matching material 9 is made of a composite material obtained by mixing a metal or an oxide into a resin or various kinds of resins, and the acoustic impedance thereof is set to be in a range of 1.5 to 3 MRayl. Since acoustic impedance of the above-described transducer 1 is considered to be in a range of 20 to 30 MRayl and acoustic impedance of the living tissue in the object to be examined is considered to be about 1.5 MRayl, these settings are performed in order that the acoustic impedances of the first and second acoustic matching materials come nearer to those of the transducer 1 and the living tissue.

Mentioned as concrete examples of the above-described materials are, as the first acoustic matching material, aluminum (17 MRayl), tin (24 MRayl), lead (22 MRayl), magnesium (10 MRayl), silicon (20 MRayl), glass (13 MRayl), crystal (15 MRayl), a composite material obtained by mixing tungsten into an epoxy resin (10 MRayl), and so on. Mentioned as the second acoustic matching material 9 are plastics and rubbers such as epoxy, polyurethane, polystyrene, polyethylene, and polybiphenyl chloride.

Figure 20:
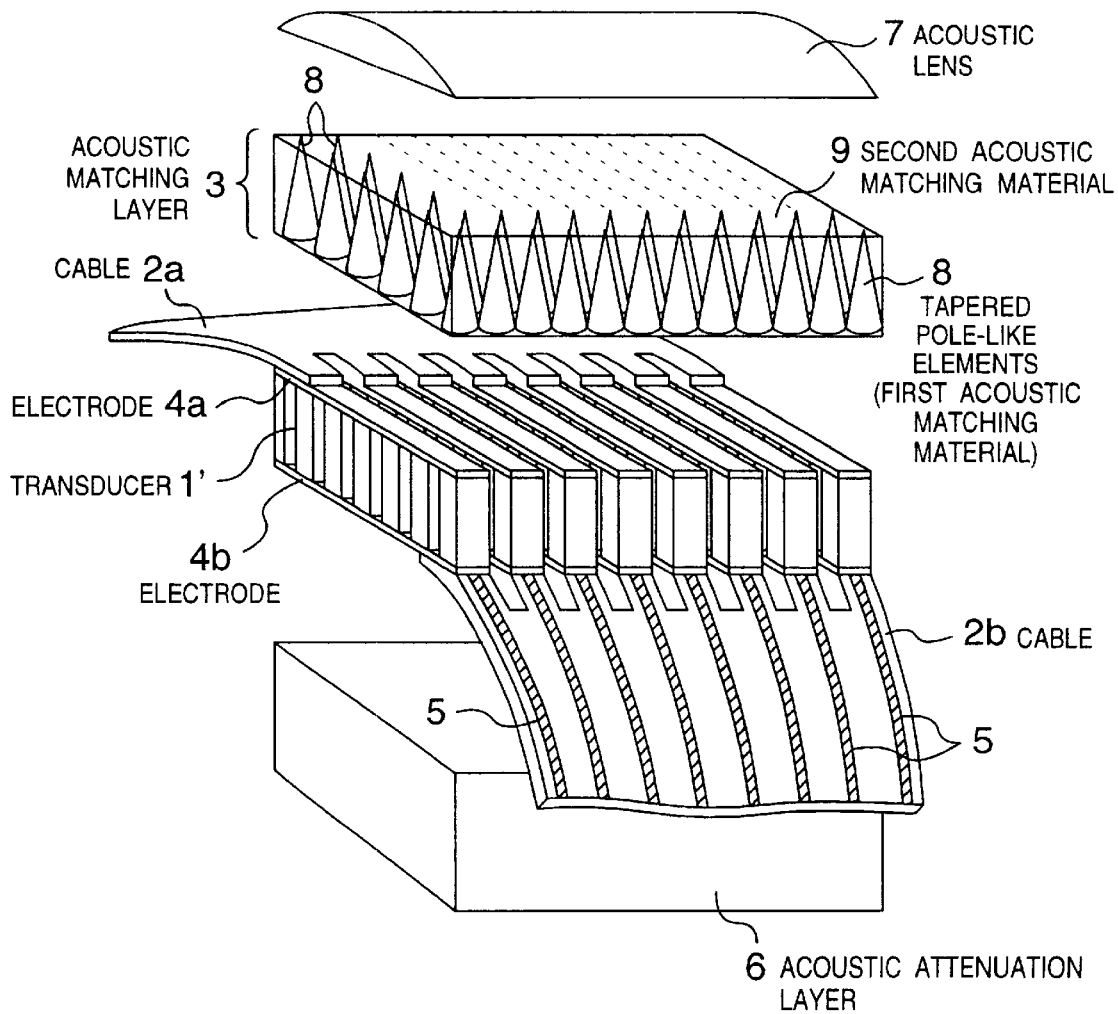
FIG. 20 is a diagram for showing another embodiment in which a pole-like transducer is used.

Also, as shown in FIG. 20, instead of the transducer 1 consisting of the strip-like transducer elements 1 in FIG. 1, it is possible to constitute the ultrasonic probe using a transducer 1' consisting of pole-like transducer elements 1'. It is also possible to employ, as the transducer 1' at this time, a composite piezoelectric medium which is constituted by arranging piezoelectric materials like, for example, PZTs in a matrix-like form and then filling spaces among the individual transducer elements 1' of the transducer 1' with a substance such as a resin (the illustration omitted). Moreover, the piezoelectric materials are not necessarily limited to the PZTs, and it is allowable to employ a piezoelectric material of a single crystalline property.

Figure 2A:
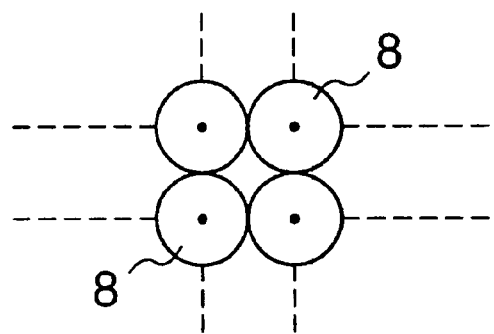
FIGS. 2A, 2B are diagrams for illustrating a first concrete example of a structure of an acoustic matching layer.
Figure 2B:
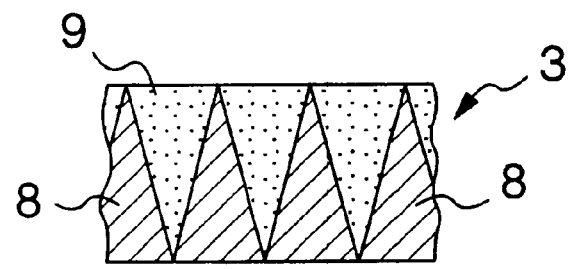

FIGS. 2A, 2B are diagrams for illustrating a first concrete example of a structure of the above-mentioned acoustic matching layer 3. In this example, the structure of the acoustic matching layer 3 is as follows: A plurality of tapered pole-like elements 8, 8, ..., which are formed with the first acoustic matching material, are formed in a form like a circular cone and arranged, as is shown in FIG. 2A, in a matrix-like form with a spacing shorter than a wavelength of the ultrasonic wave to be used. Then, spaces among the plurality of tapered pole-like elements 8, 8, ..., which are arranged in the matrix-like form, are filled with the second acoustic matching material 9, thus forming the acoustic matching layer 3. As is shown in FIG. 2B, the spaces among the plurality of tapered pole-like elements 8, 8, ... are filled with the second acoustic matching material 9, thereby making it possible to vary acoustic impedance of the acoustic matching layer 3 continuously in the thickness direction which, as shown in FIG. 1, heads from the side of the transducer 1 to the side of the object to be examined (the side of the acoustic lens 7).

Figure 3A:
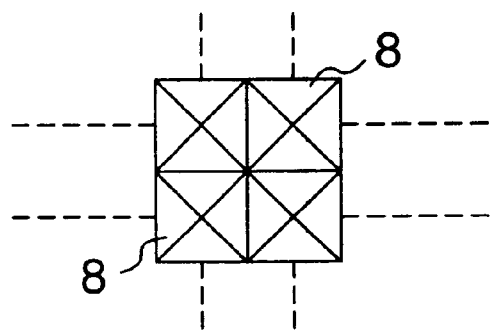
FIGS. 3A, 3B are diagrams for illustrating a second concrete example of a structure of the acoustic matching layer.
Figure 3B:
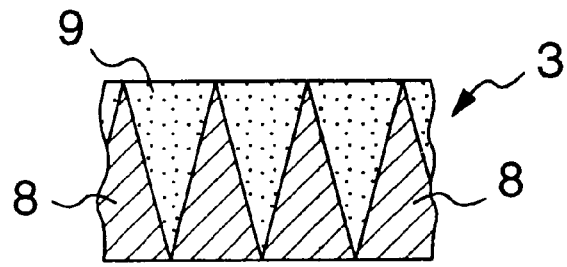

FIGS. 3A, 3B are diagrams for illustrating a second concrete example of a structure of the above-mentioned acoustic matching layer 3. In this example, the structure of the acoustic matching layer 3 is as follows: A plurality of tapered pole-like elements 8, 8, ..., which are formed with the first acoustic matching material, are formed in a form like a pyramid and arranged, as is shown in FIG. 3A, in a matrix-like form with a spacing shorter than a wavelength of the ultrasonic wave to be used. Then, spaces among the plurality of tapered pole-like elements 8, 8, ..., which are arranged in the matrix-like form, are filled with the second acoustic matching material 9, thus forming the acoustic matching layer 3. The other circumstances are the same as those in FIGS. 2A, 2B.

Figure 4A:
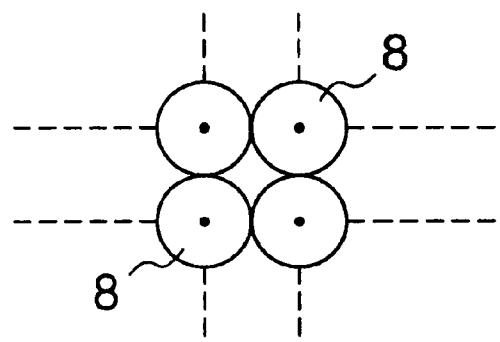
FIGS. 4A, 4B are diagrams for illustrating a third concrete example of a structure of the acoustic matching layer.
Figure 4B:
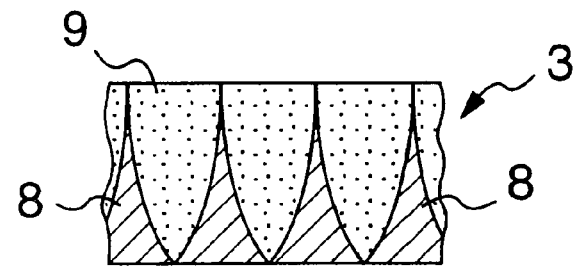

FIGS. 4A, 4B are diagrams for illustrating a third concrete example of a structure of the above-mentioned acoustic matching layer 3. In this example, the structure of the acoustic matching layer 3 is as follows: A plurality of tapered pole-like elements 8, 8, ..., which are formed with the first acoustic matching material, are formed in a form like a cone the generator of which is expressed by exponential function and are arranged, as is shown in FIG. 4A, in a matrix-like form with a spacing shorter than a wavelength of the ultrasonic wave to be used. Then, spaces among the plurality of tapered pole-like elements 8, 8, ..., which are arranged in the matrix-like form, are filled with the second acoustic matching material 9, thus forming the acoustic matching layer 3. The other circumstances are the same as those in FIGS. 2A, 2B.

Figure 5A:
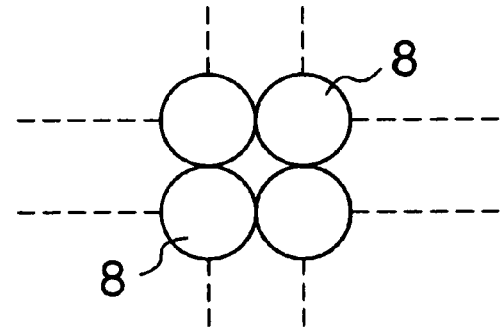
FIGS. 5A, 5B are diagrams for illustrating a fourth concrete example of a structure of the acoustic matching layer.
Figure 5B:
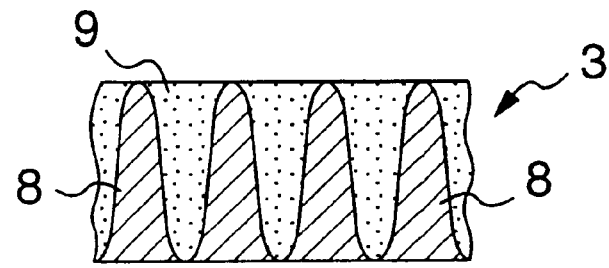

FIGS. 5A, 5B are diagrams for illustrating a fourth concrete example of a structure of the /above-mentioned acoustic matching layer 3. In this example, the structure of the acoustic matching layer 3 is as follows: A plurality of tapered pole-like elements 8, 8, ..., which are formed with the first acoustic matching material, are formed in a form like a cone the generator of which is expressed by trigonometric functions and are arranged, as is shown in FIG. 5A, in a matrix-like form with a spacing shorter than a wavelength of the ultrasonic wave to be used. Then, spaces among the plurality of tapered pole-like elements 8, 8, ..., which are arranged in the matrix-like form, are filled with the second acoustic matching material 9, thus forming the acoustic matching layer 3. The other circumstances are the same as those in FIGS. 2A, 2B.

Figure 6A:
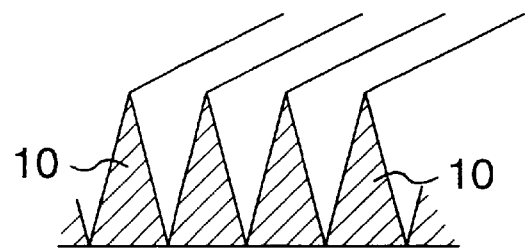
FIGS. 6A, 6B are diagrams for illustrating a fifth concrete example of a structure of the acoustic matching layer.
Figure 6B:
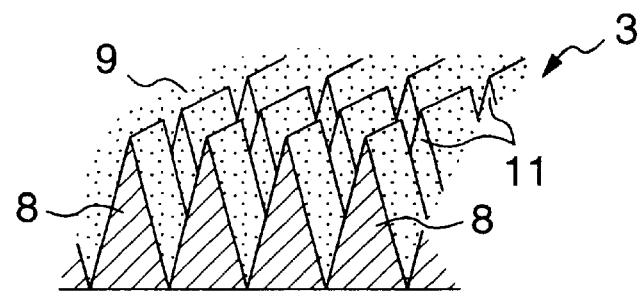

FIGS. 6A, 6B are diagrams for illustrating a fifth concrete example of a structure of the above-mentioned acoustic matching layer 3. In this example, the structure of the acoustic matching layer 3 is as follows, and a plurality of tapered pole-like elements 8, 8, ..., which are formed with the first acoustic matching material, are formed in the following way: A plurality of plate-like members 10, 10, ..., which are formed with the first acoustic matching material and, as shown in FIG. 6A, the cross sections of which are formed in a serration-like form, are cut, as shown in FIG. 6B, with a spacing shorter than a wavelength of the ultrasonic wave so that grooves 11, 11, ... are cut to the bottoms thereof, thereby forming the plurality of tapered pole-like elements 8, 8, ..... Then, the large number of tapered pole-like elements 8, 8, ... are arranged in a matrix-like form, and spaces among the large number of tapered pole-like elements 8, 8, ..., which are arranged in the matrix-like form, are filled with the second acoustic matching material 9, thus forming the acoustic matching layer 3. The other circumstances are the same as those in FIGS. 2A, 2B.

Figure 7A:
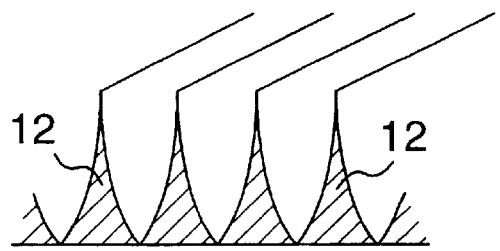
FIGS. 7A, 7B are diagrams for illustrating a sixth concrete example of a structure of the acoustic matching layer.
Figure 7B:
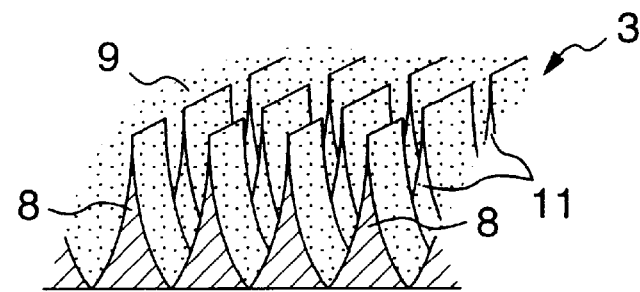

FIGS. 7A, 7B are diagrams for illustrating a sixth concrete example of a structure of the above-mentioned acoustic matching layer 3. In this example, the structure of the acoustic matching layer 3 is as follows, and a plurality of tapered pole-like elements 8, 8, ..., which are formed with the first acoustic matching material, are formed in the following way: A plurality of plate-like members 12, 12, ..., which are formed with the first acoustic matching material and, as shown in FIG. 7A, the cross sections of which are formed in an exponential function-like form, are cut, as shown in FIG. 7B, with a spacing shorter than a wavelength of the ultrasonic wave so that grooves 11, 11, ... are cut to the bottoms thereof, thereby forming the plurality of tapered pole-like elements 8, 8, ..... Then, the large number of tapered pole-like elements 8, 8, ... are arranged in a matrix-like form, and spaces among the plurality of tapered pole-like elements 8, 8, ..., which are arranged in the matrix-like form, are filled with the second acoustic matching material 9, thus forming the acoustic matching layer 3. The other circumstances are the same as those in FIGS. 2A, 2B.

Figure 8A:
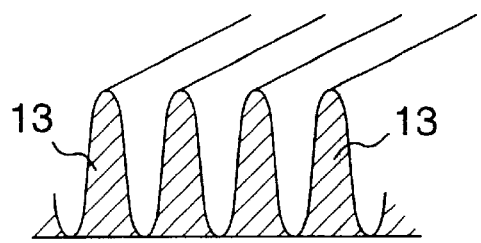
FIGS. 8A, 8B are diagrams for illustrating a seventh concrete example of a structure of the acoustic matching layer.
Figure 8B:
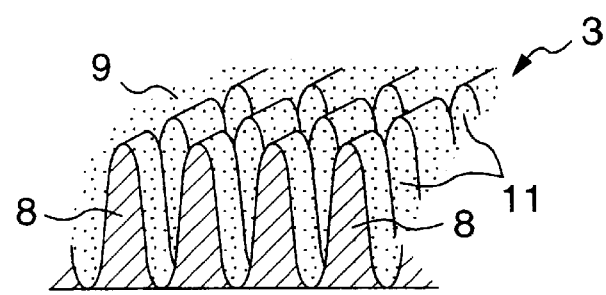

FIGS. 8A, 8B are diagrams for illustrating a seventh concrete example of a structure of the above-mentioned acoustic matching layer 3. In this example, the structure of the acoustic matching layer 3 is as follows, and a plurality of tapered pole-like elements 8, 8, ..., which are formed with the first acoustic matching material, are formed in the following way: A plurality of plate-like members 13, 13, ..., which are formed with the first acoustic matching material and, as shown in FIG. 8A, the cross sections of which are formed in a trigonometric function-like form, are cut, as shown in FIG. 8B, with a spacing shorter than a wavelength of the ultrasonic wave so that grooves 11, 11, . . . are cut to the bottoms thereof, thereby forming the plurality of tapered pole-like elements 8, 8, . . . . Then, the plurality of tapered pole-like elements 8, 8, . . . are arranged in a matrix-like form, and spaces among the plurality of tapered pole-like elements 8, 8, . . . , which are arranged in the matrix-like form, are filled with the second acoustic matching material 9, thus forming the acoustic matching layer 3. The other circumstances are the same as those in FIGS. 2A, 2B.

Figure 9A:
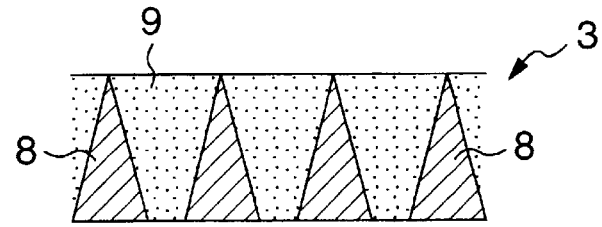
FIGS. 9A, 9B, 9C are diagrams for illustrating modified examples of arrangement of tapered pole-like elements in the above-described acoustic matching layer.
Figure 9B:
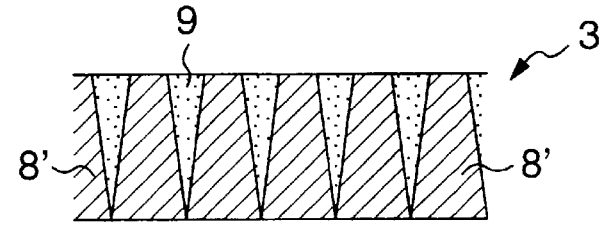
Figure 9C:
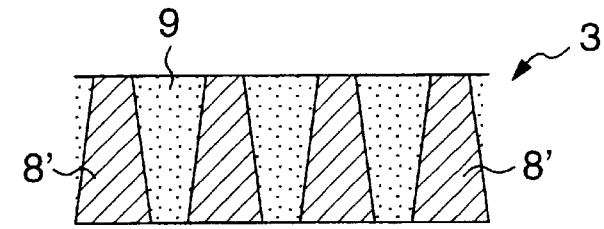

Incidentally, in the example shown in FIGS. 2A, 2B, it is assumed that the circular cone-like tapered pole-like elements 8, 8, . . . are arranged in such a manner that, at the bottoms thereof, they neighbor on each other with no space therebetween. In the present invention, however, the arrangement is not limited to this. It is allowable that, as shown in FIG. 9A, the above-mentioned circular cone-like tapered pole-like elements 8, 8, . . . are arranged in such a manner that the bottoms thereof are separated with each other by an appropriate spacing. It is also allowable that, as shown in FIG. 9B, the tip of the circular cone-like tapered pole-like element 8 is cut off by an appropriate length so as to form a tapered pole-like element 8' the cross section of which is a trapezoid-like form, and a plurality of these tapered pole-like elements 8', 8', . . . are arranged neighboring on each other, i.e. in much the same way as in FIG. 2B. Moreover, it is allowable that, as shown in FIG. 9C, the above-mentioned plurality of these tapered pole-like elements 8', 8', . . . are arranged in such a manner that the bottoms thereof are separated with each other by an appropriate spacing. These modified examples make it possible to adjust, in various ways, a state which allows acoustic impedance of the acoustic matching layer 3 to be varied continuously in the thickness direction. Additionally, these modified examples are not limited to the example shown in FIGS. 2A, 2B, and the above-described modified arrangements are applicable to various kinds of acoustic matching layers 3 shown in FIGS. 3A, 3B to 8A, 8B.

Figure 18:
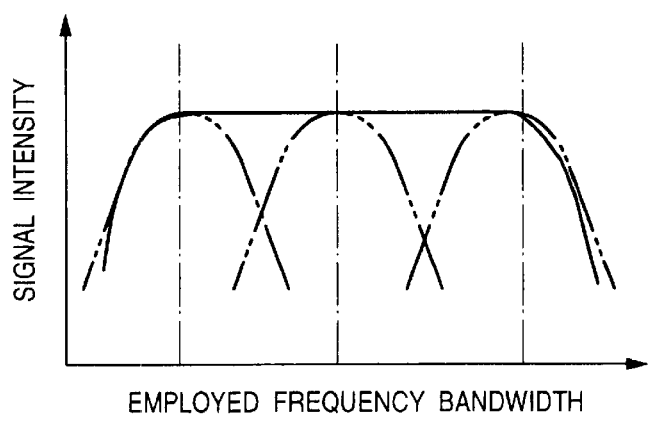
FIG. 18 is a graph for indicating a distribution characteristic of frequency-signal intensity in the ultrasonic probe according to the present invention.
Figure 19:
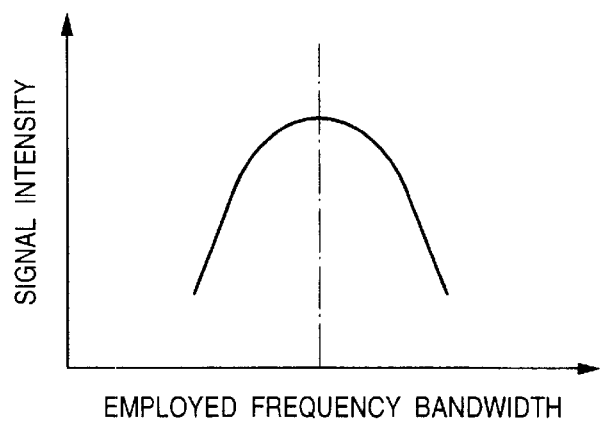
FIG. 19 is a graph for indicating a distribution characteristic of frequency-signal intensity in an ultrasonic probe in the prior art.

The above-described various kinds of acoustic matching layers 3 shown in FIGS. 2A, 2B to 8A, 8B make it possible to vary the acoustic impedances thereof continuously in the thickness direction which, as shown in FIG. 1, heads from the side of the transducer 1 to the side of the object to be examined (the side of the acoustic lens 7). Namely, the acoustic matching layers 3 enable the acoustic impedances thereof to be varied continuously from the value for the transducer 1 to the value for the living tissue of the object to be examined, thus making it possible to reduce a reflection of the ultrasonic wave due to a mismatch in acoustic impedance. This eventually makes it possible to cause ultrasonic waves with frequencies over a broader range to pass through, thus broadening, as shown in FIG. 18, the signal intensity distribution as compared with the employed frequency bandwidth. This further makes it possible to broaden a frequency bandwidth through which the ultrasonic waves are able to pass effectively and allows them to pass through a frequency bandwidth being off the central frequency, thus enlarging frequencies available for the ultrasonic probe.

Explained next, referring to FIG. 10 and FIGS. 11A to 11C, is a method of manufacturing the ultrasonic probe as a related invention of the ultrasonic probe constituted as above. First, a plurality of tapered pole-like elements 8, 8, . . . are formed with the first acoustic matching material (step ① in FIG. 10). The first acoustic matching material, as described earlier, is composed of a material the acoustic impedance of which is equal to or lower than that of the transducer 1. The above-mentioned tapered pole-like element 8, as shown in FIG. 11A, is formed in such a manner that the cross sectional area thereof or the volume thereof is larger on the side of the transducer 1 shown in FIG. 1 and is smaller on the side of the object to be examined (the side of the acoustic lens 7), and is arranged in a plurality in a matrix-like form with a spacing shorter than a wavelength of the ultrasonic wave. In FIG. 11A, the above-described plurality of tapered pole-like elements 8, 8, . . . are formed in a form like a cone the generator of which is expressed by exponential function, as is the case with FIGS. 4A, 4B. Incidentally, the tapered pole-like elements 8, 8, . . . may be formed by whatever method. For example, it is allowable to grind an upper surface of a base member 14 by means of the machining thereof.

Then, spaces among the plurality of tapered pole-like elements 8, 8, . . . , which are formed with the above-described first acoustic matching material, are filled with the second acoustic matching material 9, and the second acoustic matching material 9 is hardened (step ②). The second acoustic matching material 9 is composed of a material the acoustic impedance of which is equal to or higher than that of the living tissue in the object to be examined. As is shown in FIG. 11B, this step fills, with the second acoustic matching material 9, all the spaces among the plurality of tapered pole-like elements 8, 8, . . . which are formed with the first acoustic matching material.

Moreover, the whole structure, which is formed by filling, with the second acoustic matching material 9, all the spaces among the plurality of tapered pole-like elements 8, 8, . . . which are formed with the first acoustic matching material, is finished to a predetermined thickness, thereby completing the acoustic matching layer 3 (step ③). Finishing the whole structure into the predetermined thickness by, for example, grinding a lower surface of the base member 14 shown in FIG. 11A, this step completes the acoustic matching layer 3 composed of a composite material which, as is shown in FIG. 11C, consists of the first acoustic matching material 8 and the second acoustic matching material 9.

After that, the above-mentioned acoustic matching layer 3 is fixed on the front side of the transducer 1 (step ④). Namely, as shown in FIG. 1, with the bottoms of the plurality of tapered pole-like elements 8, 8, . . . directed toward the side of the transducer 1 and with the tips thereof directed toward the side of the acoustic lens 7, the acoustic matching layer 3 is fixed in adhesion using, for example, an adhesive in such a manner as to cover the front side of the transducer 1. This step manufactures a basic part of the ultrasonic probe.

Figure 12:
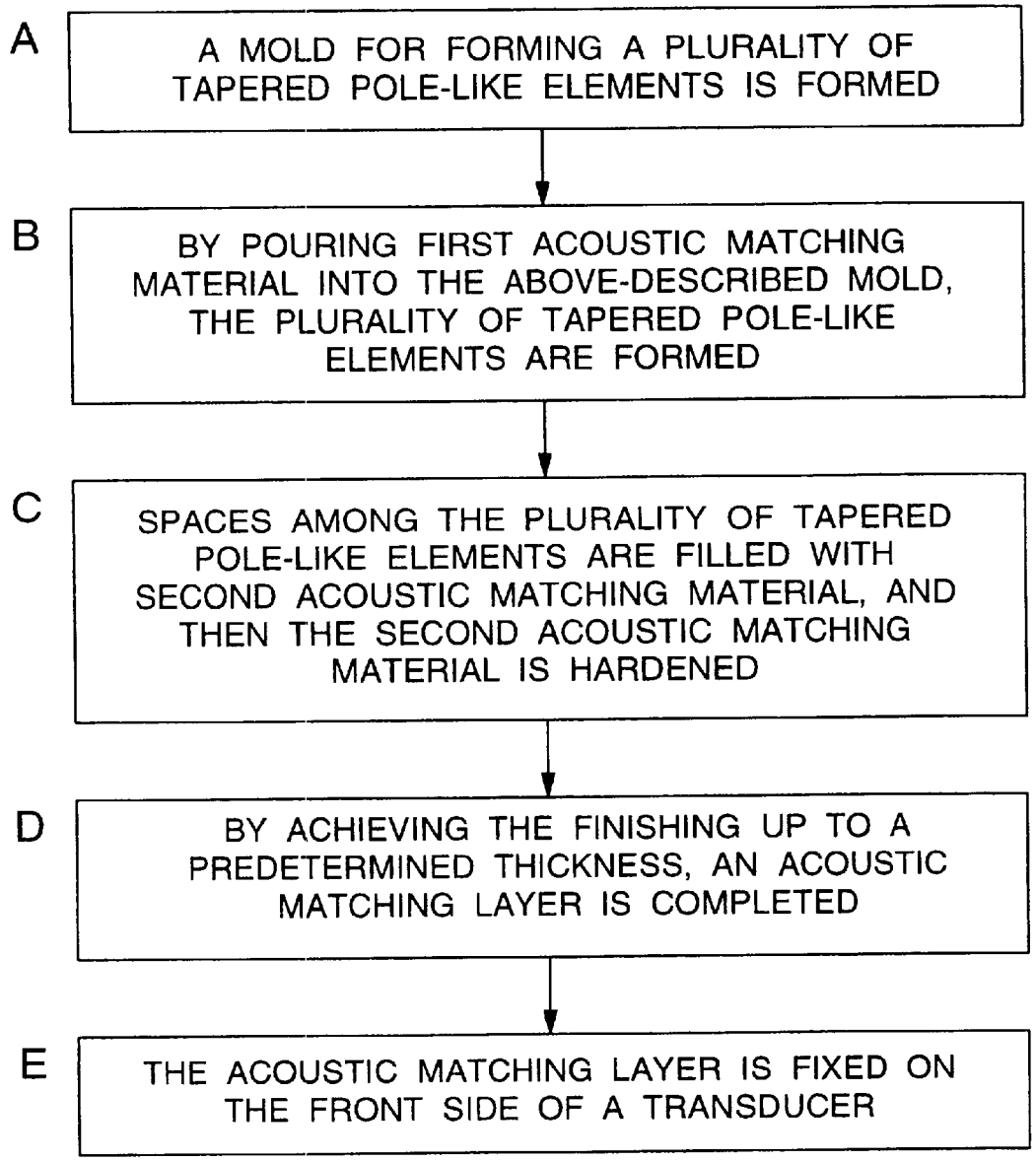
FIG. 12 is a flow chart for explaining another example of a method of manufacturing the above-described ultrasonic probe.
Figure 13A:
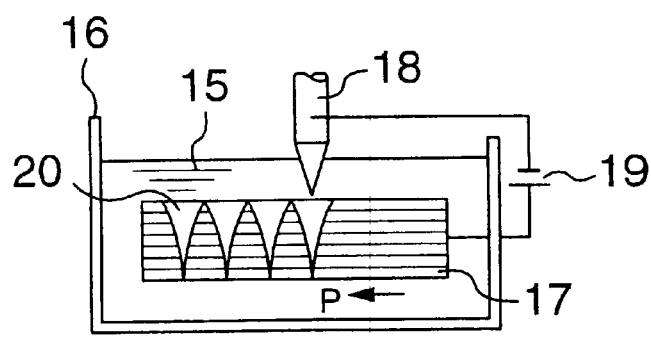
FIGS. 13A to 13E are flow diagrams for illustrating the procedure in FIG. 12.
Figure 13B:
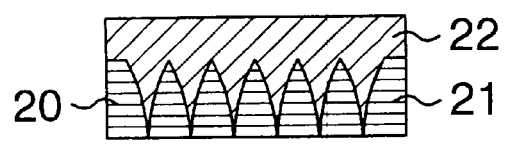
Figure 13C:
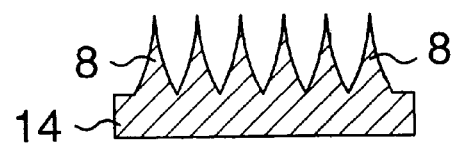

Explained next, referring to FIG. 12 and FIGS. 13A to 13E, is another method of manufacturing the ultrasonic probe equally as a related invention thereof. Formed first is a mold for forming a plurality of tapered pole-like elements 8, 8, . . . , which are to be formed in such a manner that, as shown in FIG. 13C, the cross sectional area thereof or the volume thereof is larger on the side of the transducer and is smaller on the side of the object to be examined and are then to be arranged in a matrix-like form with a spacing shorter than a wavelength of the ultrasonic wave (step A in FIG. 12).

Explained below, as a concrete example for forming this mold, is a method in which an electrical discharge machining is employed. As shown in FIG. 13A, a mold material 17 is located inside an electrical discharge machining bath 16 into which an electrical discharge machining oil 15 is poured. An electrical discharging axis 18 is positioned approximately perpendicularly to an upper surface of the mold material 17, and a voltage is applied between the mold material 17 and the electrical discharging axis 18 through the electrical discharge machining oil 15 from a power supply 19, thus machining, in sequence, a predetermined configuration of hole 20 along the above-mentioned electrical discharging axis 18. At this time, the above-described mold material 17 is moved in sequence in a direction indicated by an arrow P. In this way, with the mold material 17 being moved in sequence, the hole machining is continued until a predetermined number of holes 20, 20, . . . are bored in a matrix-like form. Then, the mold material 17, for which the hole machining is over, is extracted from the electrical discharge machining bath 16, thereby, as shown in FIG. 13B, forming a mold 21 for forming the tapered pole-like elements 8, 8, . . . .

Then, by pouring the first acoustic matching material, the acoustic impedance of which is equal to or lower than that of the transducer, into the mold 21 formed as described above, the plurality of tapered pole-like elements 8, 8, . . . , which are arranged in the matrix-like form, are formed (step B). At this time, as is shown in FIG. 13B, a raw material 22 of the first acoustic matching material is poured into the holes 20, 20, . . . in the above-mentioned mold 21, and is hardened, and after that is extracted from the mold 21, thereby, as shown in FIG. 13C, forming the plurality of tapered pole-like elements 8, 8, . . . .

Figure 13D:
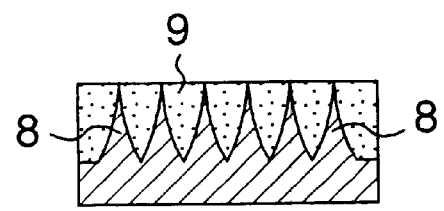

Next, spaces among the plurality of tapered pole-like elements 8, 8, . . . , which are formed with the first acoustic matching material, are filled with the second acoustic matching material 9 the acoustic impedance of which is equal to or higher than that of the living tissue in the object to be examined, and the second acoustic matching material 9 is hardened (step C). As is shown in FIG. 13D, this step fills, with the second acoustic matching material 9, all the spaces among the plurality of tapered pole-like elements 8, 8, . . . which are formed with the first acoustic matching material.

Figure 13E:
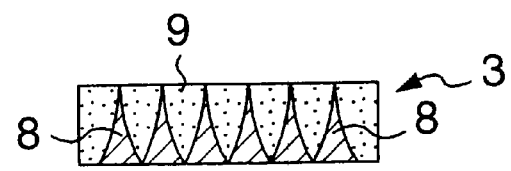

Moreover, the whole structure, which is formed by filling, with the second acoustic matching material 9, all the spaces among the plurality of tapered pole-like elements 8, 8, . . . which are formed with the first acoustic matching material, is finished to a predetermined thickness, thereby completing the acoustic matching layer 3 (step D). Finishing the whole structure into the predetermined thickness by, for example, grinding a lower surface of a base member 14 shown in FIG. 13C, this step completes the acoustic matching layer 3 composed of a composite material which, as is shown in FIG. 13E, consists of the first acoustic matching material 8 and the second acoustic matching material 9.

After that, the above-mentioned acoustic matching layer 3 is fixed on the front side of the transducer 1 (step E). Namely, as shown in FIG. 1, with the bottoms of the plurality of tapered pole-like elements 8, 8, . . . directed toward the side of the transducer 1 and with the tips thereof directed toward the side of the acoustic lens 7, the acoustic matching layer 3 is fixed in adhesion using, for example, an adhesive in such a manner as to cover the front side of the transducer 1. This step manufactures a basic part of the ultrasonic probe.

Figure 14A:
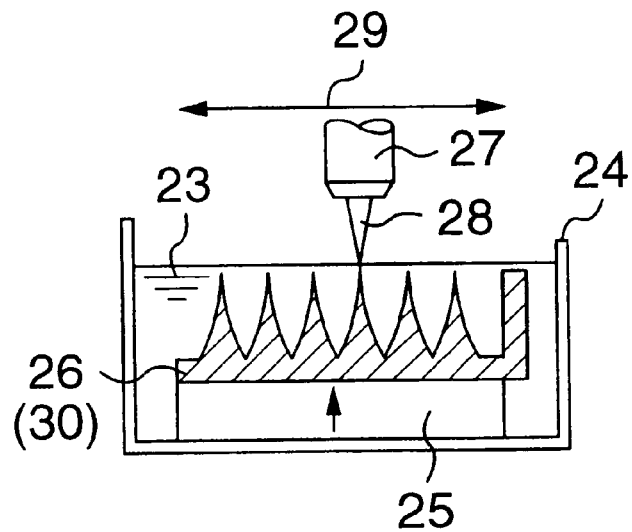
FIGS. 14A to 14C are diagrams for illustrating another example of a concrete example of steps A, B in FIG. 12.
Figure 14B:
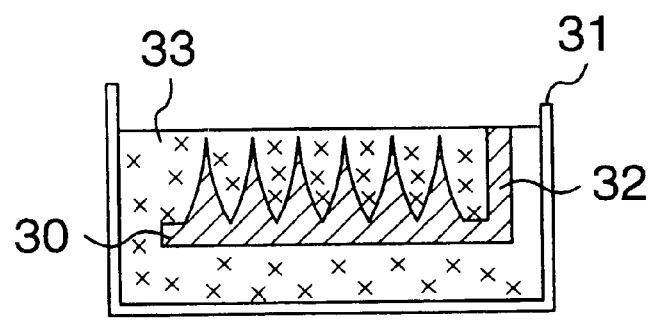
Figure 14C:
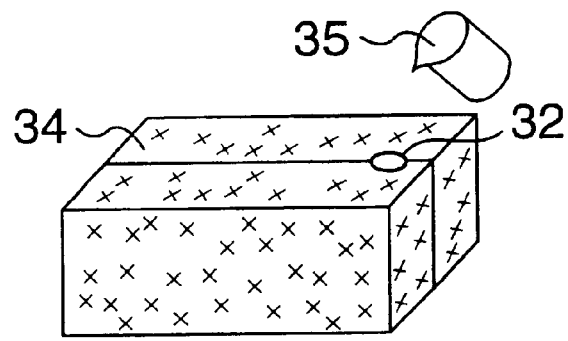

FIGS. 14A to 14C are diagrams for illustrating another example of a concrete example of the steps A, B in FIG. 12. In this example, a mold for forming the plurality of tapered pole-like elements is formed using an optical molding method. Namely, as shown in FIG. 14A, an up-and-down table 25 is located inside a resin bath 24 into which an optical hardening resin 23 is poured, and a mold material 26 is set on an upper surface of the up-and-down table 25. In this state, a laser oscillator 27 is positioned approximately perpendicularly to an upper surface of the above-mentioned mold material 26. Then, ultraviolet, for example, laser light 28 is oscillated with the light beam being converged by an objective lens. Next, the configuration is formed for each layer by scanning the laser oscillator 27 in a horizontal direction along a predetermined path 29, and at the same time the above-described up-and-down table 25 is lowered in sequence. This process forms a mask 30 for forming the plurality of tapered pole-like elements.

Next, as shown in FIG. 14B, the above-described mask 30 thus formed is placed in a pouring vessel 31. Moreover, while holding the mask 30 so that a casting hole 32 to be used later can be ensured, a heat-resistant raw material 33 is poured into the pouring vessel 31, and then the heat-resistant raw material 33 is hardened. In addition, when the heat-resistant raw material 33 is completely hardened, the mask 30 confined within the heat-resistant raw material 33 is melted, thereby forming the mold for forming the plurality of tapered pole-like elements.

After that, as shown in FIG. 14C, a mold 34 formed as described above is taken out of the pouring vessel 31, and a raw material 35 of the first acoustic matching material is poured into the mold 34 from the casting hole 32 formed therein. Then, the raw material 35 is hardened within the mold 34, thereby, as is the case with FIG. 13C, forming the plurality of tapered pole-like elements 8, 8, . . . .

Figure 15A:
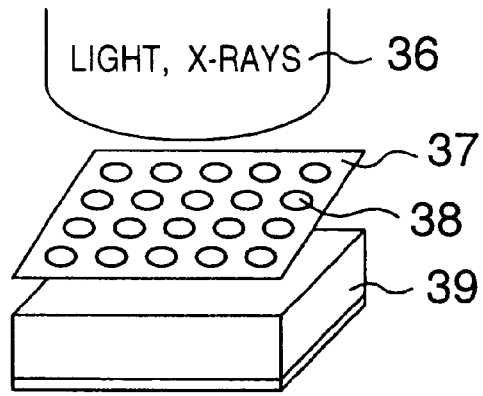
FIGS. 15A to 15E are diagrams for illustrating still another example of a concrete example of the steps A, B in FIG. 12.
Figure 15B:
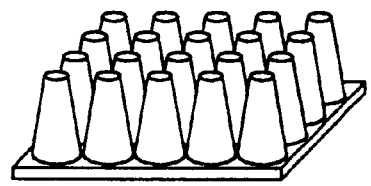

FIGS. 15A to 15E are diagrams for illustrating still another example of a concrete example of the steps A, B in FIG. 12. In this example, a mold for forming the plurality of tapered pole-like elements is formed using an optical lithography or an X-ray lithography. Namely, as shown in FIG. 15A, a resist 39 is exposed to light or X-rays from a light source or an X-ray source 36 through patterns 38 on a mask 37, thus performing the patterning. Then, as shown in FIG. 15B, the resist 39, to which the exposure is over, is developed so as to eliminate a resist 39 except for a resist 39 onto which the patterns 38 are projected.

Figure 15C:
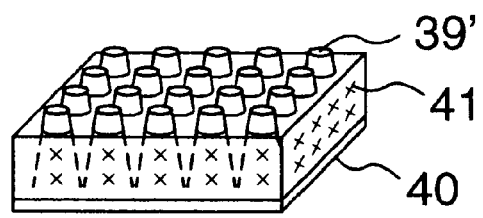
Figure 15D:
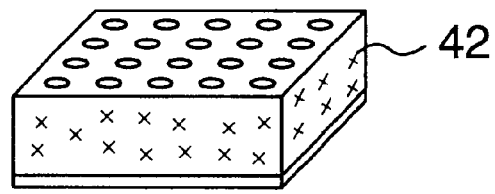
Figure 15E:

Next, as shown in FIG. 15C, using as a base a conductive substrate 40 on which the remaining resist 39' is fixed, a metal 41 is deposited by means of the plating. Moreover, as shown in FIG. 15D, the remaining resist 39' is eliminated, thereby forming a mold 42 for forming the plurality of tapered pole-like elements. After that, as shown in FIG. 15E, a raw material 43 of the first acoustic matching material is poured into the mold 42 formed as described above, and is hardened, and is then extracted from the mold 42, thereby, as is the case with FIG. 13C, forming the plurality of tapered pole-like elements 8, 8, . . . .

Figure 16A:
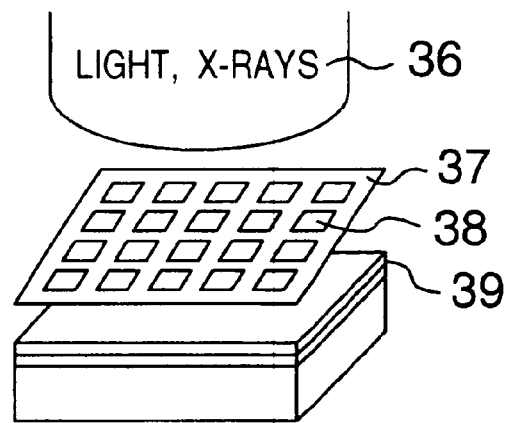
FIGS. 16A to 16E are diagrams for illustrating an even further example of a concrete example of the steps A, B in FIG. 12.
Figure 16B:
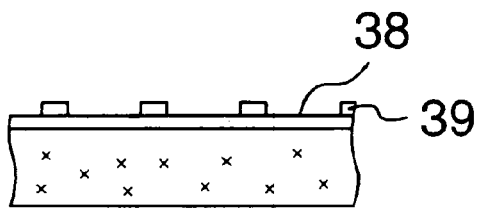
Figure 16C:
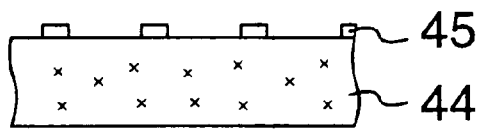

FIGS. 16A to 16E are diagrams for illustrating an even further example of a concrete example of the steps A, B in FIG. 12. In this example, too, as is the case with the above-mentioned example, a mold for forming the plurality of tapered pole-like elements is formed using an optical lithography or an X-ray lithography. Namely, as shown in FIG. 16A, a resist 39 is exposed to light or X-rays from a light source or an X-ray source 36 through patterns 38 on a mask 37, thus performing the patterning. Then, as shown in FIG. 16B, the resist 39, to which the exposure is over, is developed so as to leave and form a resist 39 onto which the patterns 38 are projected. Next, as shown in FIG. 16C, using the remaining resist 39 as a mask further, an oxide film 45 on a substrate 44 is eliminated by means of the etching.

Figure 16D:
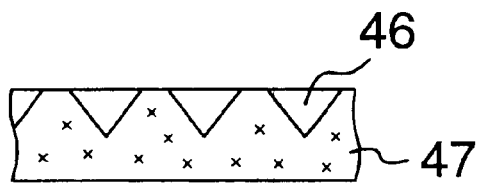
Figure 16E:
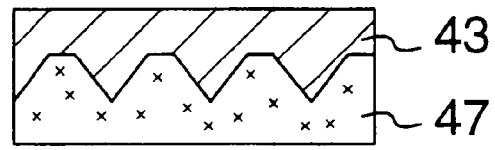

Moreover, as shown in FIG. 16D, by employing a substance, such as a single crystal silicon, as the above-mentioned substrate 44, it becomes possible to perform an anisotropy etching using an alkaline aqueous solution. For example, holes 46 in a pyramid-like form are formed so as to form a mold 47 for forming the large number of tapered pole-like elements. After that, as shown in FIG. 16E, a raw material 43 of the first acoustic matching material is poured into the mold 47 formed as described above, and is hardened, and is then extracted from the mold 47, thereby, as is the case with FIG. 13C, forming the plurality of tapered pole-like elements 8, 8, . . . .

Figure 17:
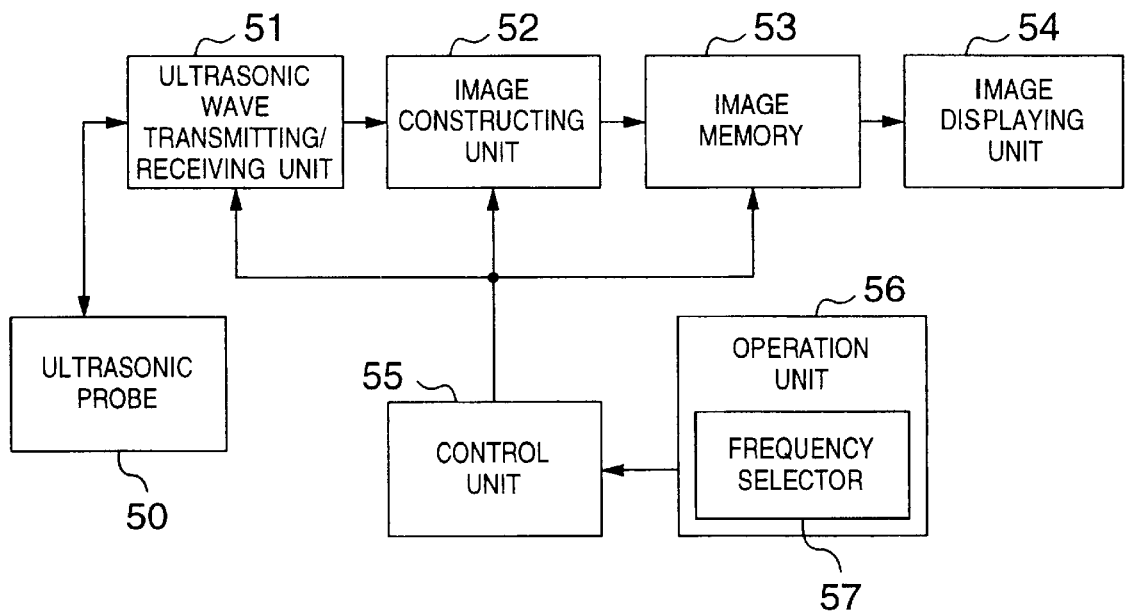
FIG. 17 is a block diagram for indicating a whole constitution of an ultrasonic diagnostic apparatus using the ultrasonic probe constituted as above according to the present invention.

FIG. 17 is a block diagram for indicating a whole constitution of an ultrasonic diagnostic apparatus using the ultrasonic probe constituted as above according to the present invention. Namely, as shown in FIG. 17, in the ultrasonic diagnostic apparatus which comprises an ultrasonic probe 50 for transmitting and receiving ultrasonic wave to and from the inside of an object to be examined, an ultrasonic wave transmitting/receiving unit 51 which not only drives a transducer in the ultrasonic probe 50 and causes it to generate the ultrasonic wave but also receives the reflected wave, an image constructing unit 52 for inputting a wave reception signal from the ultrasonic wave transmitting/receiving unit 51 so as to perform the imaging processing, an image memory 53 which not only temporarily stores data from the image constructing unit 52 but also performs the conversion so that an arbitrary display is possible, an image displaying unit 54 for reading out image data from the image memory 53 so as to display the image, and a control unit 55 for controlling the above-mentioned constitution components, an ultrasonic probe described in any one of FIG. 1 to FIGS. 9A to 9C is employed as the above-described ultrasonic probe 50, and at the same time a frequency selector 57 for causing the ultrasonic wave to be transmitted and received in a specific frequency bandwidth is provided inside an operation unit 56 for inputting various kinds of operation commands into the above-described control unit 55.

According to the ultrasonic diagnostic apparatus constituted as above, an ultrasonic probe described in any one of FIG. 1 to FIGS. 9A to 9C is employed as the above-described ultrasonic probe 50. This, as shown in FIG. 18, enables the signal intensity distribution to be broadened as compared with the employed frequency bandwidth. This condition further makes it possible to broaden a frequency bandwidth through which the ultrasonic wave are able to pass effectively and allows them to pass through a frequency bandwidth being off the central frequency, thus enlarging frequencies available for the ultrasonic diagnostic apparatus. Also, providing the frequency selector 57 inside the operation unit 56, through an operation of the frequency selector 57, makes it possible to specify what frequency bandwidth the above-described ultrasonic probe 50 is used in. This allows a single ultrasonic probe 50 to be utilized in a broader frequency range without being replaced, although, in the prior art, an ultrasonic probe to be used is replaced one by one depending on differences in the frequency bandwidth employed. Accordingly, it becomes possible to enhance an efficiency in the ultrasonic diagnosis.

The present invention is not limited to the embodiments disclosed above, but rather includes a variety of modifications involved within the scope of the following claims, too.

What is claimed is:

1. An ultrasonic probe, comprising:
   a group of transducers which transmits an ultrasonic wave and receives a reflected wave of said ultrasonic wave transmitted;
   a cable connected with a group of electrodes of said group of transducers; and
   an acoustic matching layer which is fixed on a front surface side of said group of transducers and the acoustic impedance of which is varied continuously in a thickness direction.

2. The ultrasonic probe as claimed in claim 1, wherein said acoustic matching layer comprises;
   a first matching portion formed with first acoustic matching material, acoustic impedance of said first acoustic matching material being equal to or lower than that of said group of transducers, said first matching portion having a plurality of small segment portions arranged in a matrix-like form with a spacing shorter than a wavelength of the ultrasonic wave to be transmitted, each of said small segment portions being formed in such a manner that the volume thereof becomes smaller gradually in a direction which heads from said group of transducers toward an object to be examined; and
   a second matching portion formed with second acoustic matching material, acoustic impedance of said second acoustic matching material being equal to or higher than that of a living tissue in the object to be examined, said second matching portion being buried in such a manner as to fill a space in said first matching portion.

3. The ultrasonic probe as claimed in claim 2, wherein said first matching portion comprises a plurality of pole-like elements, said plurality of pole-like elements being formed in such a manner that they are tapered gradually in the direction which heads from said group of transducers toward the object to be examined.

4. The ultrasonic probe as claimed in claim 1, wherein said group of transducers are formed by arranging a plurality of strip-like transducers in a row-like form with a predetermined spacing.

5. The ultrasonic probe as claimed in claim 1, wherein said group of transducers are formed by arranging a plurality of pole-like transducers in a matrix-like form with a predetermined spacing.

6. The ultrasonic probe as claimed in claim 1, wherein said acoustic matching layer has a value of acoustic impedance which is, on the front surface side of said group of transducers, close to a value of acoustic impedance of said group of transducers and is, on a side of an object to be examined, close to a value of acoustic impedance of the object to be examined, said value of acoustic impedance being varied in the thickness direction continuously from a value close to the value of acoustic impedance of said group of transducers to a value close to the value of acoustic impedance of the object to be examined.

7. An ultrasonic probe, which transmits and receives an ultrasonic wave in such a manner as to be in contact with an object to be examined so that an ultrasonic image is obtained concerning a diagnosis part in the object to be examined, comprising:
   a group of transducers formed, as a whole, in a substantially flat form by locating a plurality of transducers in a row-like or matrix-like form, each of said plurality of transducers being formed in a strip-like or pole-like form and, by an input of an electrical signal, performing a mechanical vibration so as to generate the ultrasonic wave;
   a group of electrodes comprising a plurality of electrodes in a plurality number of rows with a predetermined spacing, each of said plurality of electrodes being formed in a row-like form and connecting, as a row, at least one strip-like transducer or one pole-like transducer with both upper and lower surfaces of said plurality of transducers;

a cable for inputting and outputting an electrical signal into and from said group of electrodes;

an acoustic attenuation layer located on a lower surface side of said group of transducers and preventing ultrasonic waves, which are generated from lower surfaces of said group of transducers, from being reflected back again to and inputted into said group of transducers;

an acoustic matching layer having a predetermined thickness, formed as a whole in a substantially flat form, located on an upper surface side of said transducers, and having an acoustic impedance which is continuously varied in a thickness direction thereof, ultrasonic waves in a desired frequency bandwidth, which are generated from said group of transducers, being allowed to pass through the object to be examined; and an acoustic lens for converging the ultrasonic waves, which are generated from said group of transducers, onto a desired part of concern in the object to be examined.

8. An ultrasonic diagnostic apparatus, comprising:

an ultrasonic probe which has a group of transducers for transmitting and receiving ultrasonic waves and an acoustic matching layer the acoustic impedance of which is varied continuously in a thickness direction;

an ultrasonic wave transmitting/receiving unit which drives said group of transducers to generate the ultrasonic waves and receives reflected waves;

an image constructing unit for inputting a wave reception signal from said ultrasonic wave transmitting/receiving unit so as to perform an image processing;

an image memory which temporarily stores data from said image constructing unit and performs the conversion so that an arbitrary display is possible;

an image displaying unit for fetching image data from said image memory so as to perform an image display;

a frequency selector for causing the ultrasonic wave to be transmitted and received in a specific frequency bandwidth; and a control unit for controlling each of said constitution components.

9. The ultrasonic diagnostic apparatus as claimed in claim 8, wherein said acoustic matching layer comprises;

a first matching portion formed with first acoustic matching material, an acoustic impedance of said first acoustic matching material being equal to or lower than that of said group of transducers, said first matching portion having a plurality of small segment portions arranged in a matrix-like form with a spacing shorter than a wavelength of an ultrasonic wave to be transmitted, each of said small segment portions being formed in such a manner that the volume thereof becomes smaller gradually in a direction which heads from said group of transducers toward an object to be examined; and a second matching portion formed with second acoustic matching material, an acoustic impedance of said second acoustic matching material being equal to or higher than that of a living tissue in the object to be examined, said second matching portion being buried in such a manner as to fill a space in said first matching portion.

10. The ultrasonic diagnostic apparatus as claimed in claim 9, wherein said first matching portion comprises a plurality of pole-like elements, said plurality of pole-like elements being formed in such a manner that they are tapered gradually in the direction which heads from said group of transducers toward the object to be examined.

* * * * *